United States Patent
Agnew et al.

(10) Patent No.: US 10,117,849 B2
(45) Date of Patent: Nov. 6, 2018

(54) MONENSIN WATER DISPERSIBLE GRANULES BY WET GRANULATION

(71) Applicant: Elanco US Inc., Indianapolis, IN (US)

(72) Inventors: Kim Ewing Melville Agnew, Auckland (NZ); Constantine Paul Benikos, Woronora Heights (AU); William Austin Hewitt, Auckland (NZ); Edward John Key, Nelson (NZ); John Malcolm Lloyd, Nelson (NZ)

(73) Assignee: Elanco US, Inc., Greenfield, IN (US)

( * ) Notice: Subject to any disclaimer, the term of this patent is extended or adjusted under 35 U.S.C. 154(b) by 0 days.

(21) Appl. No.: 15/556,654

(22) PCT Filed: Apr. 22, 2016

(86) PCT No.: PCT/US2016/028932
§ 371 (c)(1),
(2) Date: Sep. 8, 2017

(87) PCT Pub. No.: WO2016/176121
PCT Pub. Date: Nov. 3, 2016

(65) Prior Publication Data
US 2018/0042888 A1    Feb. 15, 2018

Related U.S. Application Data

(60) Provisional application No. 62/153,592, filed on Apr. 28, 2015.

(51) Int. Cl.
*A61K 31/35* (2006.01)
*A61K 9/00* (2006.01)
*A61K 9/16* (2006.01)

(52) U.S. Cl.
CPC ............ *A61K 31/35* (2013.01); *A61K 9/0095* (2013.01); *A61K 9/1611* (2013.01); *A61K 9/1623* (2013.01); *A61K 9/1629* (2013.01); *A61K 9/1694* (2013.01)

(58) Field of Classification Search
CPC .... A61K 31/35; A61K 9/0095; A61K 9/0623; A61K 9/1694; A61K 9/1611; A61K 9/1629
See application file for complete search history.

(56) References Cited

U.S. PATENT DOCUMENTS

| | | | | |
|---|---|---|---|---|
| 3,475,375 A | * | 10/1969 | Yates | ..................... B01J 20/103 106/18.11 |
| 5,443,764 A | * | 8/1995 | Lloyd | ..................... A01N 25/14 264/140 |
| 5,874,103 A | | 2/1999 | Moore et al. | |
| 2002/0032541 A1 | | 3/2002 | Raab et al. | |

FOREIGN PATENT DOCUMENTS

| | | | |
|---|---|---|---|
| CA | 2225741 | * | 7/1996 |
| EP | 0139595 A3 | | 10/1984 |
| EP | 3110250 | * | 1/2018 |
| NZ | 272574 A | | 7/1995 |
| WO | 97/016195 A1 | | 5/1997 |
| WO | 2013/062425 A1 | | 5/2013 |

* cited by examiner

*Primary Examiner* — Shirley V Gembeh
(74) *Attorney, Agent, or Firm* — David L. Pflugh

(57) ABSTRACT

The present disclosure provides a water dispersible granule formulation comprising from about 5% to about 80% (w/w) of monensin; from about 1% to about 20% (w/w) of one or more surfactants; from about 1% to about 30% (w/w) of one or more binders; from about 1% to about 90% (w/w) of one or more fillers; and water up to about 2% (w/w). The present disclosure also provides a process for the preparation of a water dispersible monensin granule formulation. The present disclosure further provides a method of administering a therapeutically effective amount of a water dispersible monensin granule formulation to an animal.

7 Claims, No Drawings

MONENSIN WATER DISPERSIBLE GRANULES BY WET GRANULATION

The present application is a national phase entry under 35 U.S.C. § 371 of International Patent Application PCT/US2016/028932, filed on Apr. 22, 2016 and published in English as International Patent Publication WO2016/176121 A1 on Nov. 3, 2016, which claims benefit of priority to U.S. Pat. App. Ser. No. 62/153,592; filed Apr. 28, 2015; all of which are incorporated by reference in their entirety.

Monensin is an ionophore antibiotic isolated from the bacteria *Streptomyces cinnamonensis*. In veterinary medicine, monensin can be advantageously administered to animals for a variety of purposes. For example, administration of a therapeutically effective dose of monensin can be utilized for the treatment or prevention of ketosis and/or bloat, for the enhancement of milk production efficiency, for the enhancement of milk protein content in milk, for the enhancement of mineral uptake, for the enhancement of weight gain, for the enhancement of feed conversion efficiency, and the provision of desirable reproduction advantages.

Monensin is poorly soluble in water, thus it has been difficult to find adequate and practical means of administering liquid monensin to animals. Due to its poor solubility in water, monensin was traditionally administered in dry powder form in animal feeds and/or in dry liquid-milk replacer compositions. In some instances the dry powder was mixed with liquid feeds to try to provide the animal a more consistent and controlled dose. However, due to the monensin's poor solubility, the monensin would settle out of solution creating gradients of monensin concentrations in the liquid compositions on standing, such that the top layers contained ineffectually low concentrations of the monensin, while the bottom layers contained the monensin in toxic and harmful concentrations, causing poisoning of the animals fed with these compositions. Vigorous mixing was required prior to administration to ensure ingestion before substantial concentration gradients began to appear due to settling. Such dry powder compositions often do not remain evenly distributed in liquid feeds for a sufficient period of time to make them practical or safe for use in this manner.

Thus, while the dry formulations of monensin administration has been available and used for decades, it is known that animals cannot always be induced to eat dry forms of monensin. Without being bound by any theory, it is hypothesized that the dry formulations of monensin may have a taste which the animal prefers less than the monensin-free formulations. As a result, the animal may reduce its intake and ingestion of the monensin-containing combination. As hypothesized, the taste of the dry monensin formulation could be problematic to veterinary practice. For instance, the taste could decrease the intake of monensin itself and thus inhibit its therapeutic effectiveness. In addition, the taste could lower the consumption of the combined mineral mixes and feed, thus, potentially contributing to myriad other problems in animals due to the decreased intake of nourishment.

Liquid formulations of monensin are known. For example, European Patent Application No. 0,139,595 (Koffolk (1949) Ltd.) discloses a liquid monensin composition for ruminants and poultry where the antibiotic is dissolved in soluble organic solvents and in use the resulting solution is admixed with a liquid feed, a liquid vitamin concentrate, or drinking water. Liquid formulations of monensin have also been formulated as aqueous suspension concentrates. For example, New Zealand Patent No. 272574 (Eli Lilly & Company (NZ) Limited) discloses an aqueous base suspension concentrate of monensin.

Water dispersible granule formulations can offer advantages over other types of known liquid monensin formulations, such as in packaging, ease of handling, and safety. Typically, water dispersible granule formulations are free flowing, low dusting, and readily disperse in water to form a homogenous suspension of very small particles which may pass through conventional spray nozzles. New Zealand Patent No. 596,017 (Glenmark IP Limited) discloses water dispersible ionophore antibiotic granule formulations. Unfortunately, however, the water dispersible ionophore antibiotic granule formulations disclosed in Glenmark have significant shortcomings. One shortcoming is that the preferred process for the preparation of the water dispersible granules utilizes a high pressure dry granulation process (e.g., compaction). This limited process relies on the use of a high pressure dry compaction to produce a dense cake and breaking the dense cake down mechanically to produce angular chips of irregular size and shape. Angular chips of irregular size and shape are very inefficient for the end user. It is important that granules are closely sized and of reasonably consistent bulk density to enable them to be measured accurately by volume by the end user. Volumetric measurement of water dispersible granules is preferred by end users for convenience rather than having to weigh the quantity required in a field use situation. Glenmark discloses the mean particle size of the resulting granule is from about 0.15 mm to 3 mm. Such a size range of granules is very wide and as a result segregation of the product can occur during movement and transport of the containers making accurate volumetric measurement difficult because of the differences in the bulk density of the different sized fractions.

Another shortcoming is that the water dispersible ionophore antibiotic granule formulations in Glenmark instruct the use of dry disintegrants to break the compacted chips apart when added to water. Disintegrants are mainly used in the pharmaceutical industry as a component of tablets produced by the compaction of powders by high pressure tableting machines. Disintegrants are generally insoluble materials. Disintegrants swell when the dry compacted tablets or granules become wet and cause the formulations to disintegrate enabling the active ingredients to become available. Disintegrants limit the type of granulation process that can be employed. For example, disintegrants are generally unsuitable for use in wet granulation processes. The incorporation of conventional disintegrants in wet granulation processes is not a standard practice because the disintegrants swell upon contact with the water used for granulation. Upon drying of the granules, the disintegrant particles shrink, creating a void, then expand back into the void upon subsequent hydration of the granules and fail to perform effectively. Further, depending on the type of disintegrant, particle size, and quantity of the disintegrant used, the damp premix of a wet granulation process can become rubbery and unmanageable.

Therefore, there exists a need for water dispersible monensin granule formulations that do not require the use of dry disintegrants and processes for the preparation of water dispersible monensin granule formulations that utilize wet granulation processes that can prepare high quality, single pass recovery of granules of regular size and shape. Accordingly, the present disclosure provides water dispersible monensin granules and methods of manufacture that exhibit desirable properties and provides related advantages as well.

The present disclosure provides water dispersible granule formulations comprising from about 5% to about 80% (w/w)

of monensin; from about 1% to about 20% (w/w) of one or more surfactants; from about 1% to about 30% (w/w) of one or more one binders; from about 1% to about 90% (w/w) of one or more fillers; and water up to about 2% (w/w). The formulations do not require a disintegrant. The present disclosure also provides liquid formulations comprising water dispersible monensin granule formulations dispersed in water or milk, processes for the preparation of water dispersible monensin granule formulations using wet granulation processes, and methods of administering a therapeutically effective amount of water dispersible monensin granule formulations to animals. Therefore, the present disclosure demonstrates that angular chips of irregular size and shape produced by dry granulation processes using disintegrants can be overcome by utilizing wet granulation processes to prepare water dispersible monensin granules of regular size and shape.

The present disclosure provides several advantages compared to other water dispersible granule formulations. One advantage is that the process for the preparation of the water dispersible monensin granules employs wet granulation processes. The advantage of another embodiment is that disintegrants are not required in the water dispersible monensin granules of the present disclosure, as disintegrants are generally unsuitable for use in wet granulation processes. A further advantage of another embodiment is that water dispersible monensin granules prepared via wet granulation produces high single pass recovery of granules of regular size and shape, which cannot be achieved by using high pressure dry compaction, as a dense cake is produced and broken down mechanically to produce angular chips of irregular size and shape. Therefore, the present disclosure provides improved water dispersible monensin granules and improved processes for the preparation of water dispersible monensin granules. The combination of wet granulation and lack of disintegrants in the present disclosure provide a more efficient and superior alternative to other water dispersible granule formulations.

As used herein, the term "monensin" refers to monensin base, pharmaceutically acceptable salts of monensin, or other salts of monensin. The term "pharmaceutically acceptable salt" refers to an addition salt that exists in conjunction with the acidic or basic portion of monensin. Such salts include the pharmaceutically acceptable salts listed in HANDBOOK OF PHARMACEUTICAL SALTS: PROPERTIES, SELECTION AND USE, P. H. Stahl and C. G. Wermuth (Eds.), Wiley-VCH, New York, 2002 which are known to the skilled artisan. In some embodiments, "monensin" is monensin sodium.

Pharmaceutically acceptable salts of an acid addition nature are formed when monensin and any of its intermediates containing a basic functionality are reacted with a pharmaceutically acceptable acid. Pharmaceutically acceptable acids commonly employed to form such acid addition salts include inorganic and organic acids. Pharmaceutically acceptable salts of a base addition nature are formed when monensin and any of its intermediates containing an acidic functionality are reacted with a pharmaceutically acceptable base. Pharmaceutically acceptable bases commonly employed to form base addition salts include organic and inorganic bases.

In addition to pharmaceutically acceptable salts, other salts are included in the present disclosure. They may serve as intermediates in the purification of compounds or in the preparation of other pharmaceutically-acceptable salts, or are useful for identification, characterization or purification.

The amount of monensin in the formulation is adequate to achieve a therapeutic effect, as is known in the art. As used herein, the term "therapeutically effective amount" refers to an amount which gives the desired benefit to an animal and includes both treatment and prophylactic administration. The amount will vary from one individual to another and will depend upon a number of factors, including the overall physical condition of the animal and the underlying cause of the condition to be treated. The amount of monensin used for therapy gives an acceptable rate of change and maintains desired response at a beneficial level. A therapeutically effective amount of the present formulation may be readily ascertained by one of ordinary skill in the art using publicly available materials and procedures.

In some embodiments, a preferred monensin form is the sodium salt of the acid (i.e., monensin sodium), which is generally commercially available in two forms, namely a crystalline form or a mycelial form. Both the crystalline and mycelial forms of monensin are suitable for the present disclosure. The mycelial form has only about a 20% activity while the crystalline form has a potency of not less than 800 μg/mg being as a standard pharmacopoeia material (e.g., USP), which is preferred. Crystalline monensin sodium useable in this disclosure is commercially available from many sources, such as Biovet and JSC, and preferably should have a potency of not less than 900 μg/mg.

In some embodiments of the present disclosure, the amount of monensin in the formulation can vary. In some embodiments, the monensin is present in the formulation in an amount from about 5% to about 80% (w/w). In some embodiments, the monensin is present in the formulation in an amount from about 10% to about 75% (w/w). In some embodiments, the monensin is present in the formulation in an amount from about 15% to about 70% (w/w). In some embodiments, the monensin is present in the formulation in an amount from about 20% to about 65% (w/w). In some embodiments, the monensin is present in the formulation in an amount from about 25% to about 60% (w/w). In some embodiments, wherein the monensin is present in the formulation in an amount from about 30% to about 55% (w/w). In some embodiments, the monensin is present in the formulation in an amount from about 3.5% to about 50% (w/w). In some embodiments, the monensin is present in the formulation in an amount from about 40% to about 45% (w/w). In some embodiments, the monensin is present in the formulation at about 43% (w/w).

With particular reference to crystalline monensin sodium, this equates to about 43% (w/w) of commercially available monensin sodium because of impurities in the raw material (i.e., less than 100% of the material is active). In one particular embodiment of the disclosure, the monensin is crystalline monensin sodium present in an amount at about 43% (w/w), which is intended to provide a formulation with an active concentration of about 40% (w/w) such that only 1 gram of the formulation is required to provide about 400 mg per animal per day. Therefore, each kilogram of the granule formulations disclosed may contain about 400 grams of monensin.

The monensin may optionally be coated with a surfactant to improve its dispersion in water. For a water dispersible granule formulation containing a high concentration of active, a coated active is preferred. Preferred surfactants for coating include liquid surfactants such as polysorbates, polyethylene sorbitol esters (e.g., TWEEN® 80), polyethoxylated castor oil, and lecithin. An amount of about 1% (w/w) of surfactant is typically used. Coating can be done by spraying and/or mixing the surfactant with the monensin, or the surfactant can be milled together with the monensin to coat the active.

In order to achieve the desired water dispersible granule formulation of the disclosure, it has been found that it is advantageous for the monensin to have a small, relatively uniform particle size. In some embodiments, the mean particle size diameter of the monensin is less than about 30 microns and about 80% of the monensin particles are no more than about 20 microns. In some embodiments, the monensin has a mean particle size diameter from about 1 to about 25 microns and about 80% of the monensin particles are no more than about 20 microns. In some embodiments, the monensin has a mean particle size diameter from about 5 to about 20 microns. In some embodiments, the monensin has a mean particle size diameter from about 10 to about 15 microns. In some embodiments, the monensin has a mean particle size diameter from about 10 to about 12 microns. Given that current commercially available forms of monensin, such as monensin sodium, may have a particle size range from about 40 to about 90 microns, the raw material is preferably milled or micronized to a smaller particle size during manufacture of the formulation.

The formulations of the present disclosure may contain other ionophore antibiotics in addition to monensin and/or one or more further pharmaceutically active ingredients that do not interfere with or otherwise hamper the effectiveness of the monensin. Examples of such further active ingredients may include essential minerals such as copper, selenium, cobalt, iodine, zinc, boron, and manganese, to name a few.

A number of excipients are required in the formulations of the present disclosure in order to provide a successful water dispersible monensin granule formulation with the appropriate characteristics of flowability, friability, dispersability, and re-suspensibility.

A surfactant is required for wetting the monensin. Given that monensins are particularly hydrophobic, an ideal formulation must be able to maintain the wetted state of the monensin. A non-limiting list of surfactants or wetting agents useable in the formulations of the disclosure include: anionic surfactants (e.g., alkyl sulphates such as sodium lauryl sulphate, sulphonates such as sodium dodecylbenzene sulphonate, carboxylates, dioctyl sodium sulfosuccinate); cationic surfactants (e.g., quaternary ammonium salts such as benzalkonium chloride); amphoteric surfactants (e.g., alkyl betaines and cocamidoalkyl betaines); nonionic surfactants (e.g., alkyl polyglucoside, polyoxyethylene glycol sorbitan alkyl esters (or polysorbates) and alkoxylates); and combinations thereof. In some embodiments, the surfactant is nonionic. In some embodiments, the surfactant is alkyl polyglucoside. A suitable alkyl polyglucoside is $C_8$-$C_{10}$ alkyl polyglucoside. A commercially available alkyl polyglucoside suitable for this disclosure is AGNIQUE® PG 8107 (CAS Number 68515-73-1), which contains 70% (w/v) alkyl polyglucoside in an aqueous solution. AGNIQUE® PG 8107 also has wetting agent properties.

In some embodiments of the present disclosure, the amount of the surfactant in the formulation can vary. In some embodiments, the surfactant is present in the formulation in an amount from about 1% to about 20% (w/w). In some embodiments, the surfactant is present in the formulation in an amount from about 1% to about 15% (w/w). In some embodiments, the surfactant is present in the formulation in an amount from about 1% to about 10% (w/w). In some embodiments, the surfactant is present in the formulation at about 2% (w/w). In some embodiments, the surfactant is present in the formulation at about 1% (w/w).

A non-limiting list of binders suitable in the formulations of the present disclosure include: anionic binders (e.g., lignosulphonates), nonionic binders (e.g., sucrose, other sugars, molasses, and some salts such as sodium acetate) polymeric binders, and combinations thereof. In some embodiments, the binder is anionic. In some embodiments, the binder is sodium lignosulphonate, which also provides good dispersing efficiency. A commercially available sodium lignosulphonate suitable for this disclosure is Ultrazine NA (CAS Number 8061-51-6). Ultrazine NA also has dispersing agent properties.

In some embodiments of the present disclosure, the amount of the binder in the formulation can vary. In some embodiments, the binder is present in the formulation in an amount from about 1% to about 25% (w/w). In some embodiments, the binder is present in the formulation in an amount from about 5% to about 20% (w/w). In some embodiments, the binder is present in the formulation at about 12% (w/w). In some embodiments, the binder is present in the formulation at about 10% (w/w). In some embodiments, the binder is present in the formulation at about 9% (w/w). In some embodiments, the binder is present in the formulation at about 8% (w/w). In some embodiments, the binder is present in the formulation at about 7% (w/w).

A non-limiting list of fillers suitable in the formulations of the present disclosure include: lactose monohydrate, glucose, sucrose, sugars, mannitol, modified sugars, celluloses, magnesium silicate monohydrate, synthetic amorphous alumina silica and silicate, hydrous alumina silicate, and combinations thereof. In some embodiments, the filler is a combination of magnesium silicate monohydrate and amorphous alumina silicate. Magnesium silicate monohydrate is commercially available as Talc SF (Superfine) 15 (CAS Number 14807-96-6). Talc SF 15 also has anticaking agent, lubricant, and dispersing agent properties. Amorphous alumina silicate is commercially available as HARBORLITE® 200 (CAS Number 93763-70-3), which is a perlite.

In some embodiments of the present disclosure, the amount of the filler in the formulation can vary. In some embodiments, the filler is present in the formulation in an amount from about 1% to about 85% (w/w). In some embodiments, the filler is present in the formulation in an amount from about 5% to about 80% (w/w). In some embodiments, the filler is present in the formulation in an amount from about 10% to about 75% (w/w). In some embodiments, the filler is present in the formulation in an amount from about 15% to about 70% (w/w). In some embodiments, the filler is present in the formulation in an amount from about 20% to about 65% (w/w). In some embodiments, the filler is present in the formulation in an amount from about 25% to about 60% (w/w). In some embodiments, the filler is present in the formulation in an amount from about 30% to about 55% (w/w). In some embodiments, the filler is present in the formulation in an amount from about 35% to about 50% (w/w). In some embodiments, the filler is present in the formulation in an amount from about 40% to about 45% (w/w). In some embodiments, the filler is present in the formulation at about 29% (w/w). In some embodiments, the filler is present in the formulation at about 28% (w/w). In some embodiments, the filler is present in the formulation at about 27% (w/w). In some embodiments, the filler is present in the formulation at about 26% (w/w). In some embodiments, the filler is present in the formulation at about 24% (w/w). In some embodiments, the filler is present in the formulation at about 22% (w/w). In some embodiments, the filler is present in the formulation at about 20% (w/w). In some embodiments, the filler is present in the formulation at about 18% (w/w). In some embodiments, the filler is present in the formulation at about 16% (w/w). In some embodiments, the filler is present in the formulation at about 14% (w/w). In some embodiments, the filler is present in the formulation at about 12% (w/w). In some embodiments, the filler is present in the formulation at about 10% (w/w). The amount of filler added to the formulation will generally be adjusted according to the amount of monensin included in the formulation.

The formulations of the present disclosure do not require disintegrants. Disintegrants are mainly used in the pharmaceutical industry as a component of tablets produced by the compaction of powders by high pressure tableting machines. Disintegrants are generally insoluble materials. Disintegrants swell when the dry compacted tablets or granules become wet and cause the formulations to disintegrate enabling the active ingredients to become available. In some embodiments, the formulations of the present disclosure are prepared via a wet granulation process. Disintegrants are generally unsuitable for use in wet granulation processes. The incorporation of conventional disintegrants in wet granulation processes is not a standard practice because the disintegrants swell upon contact with the water used for granulation. Upon drying of the granules, the disintegrant particles shrink, creating a void, then expand back into the void upon subsequent hydration of the granules and fail to perform effectively. Further, depending on the type of disintegrant, particle size, and quantity of the disintegrant, used, the damp premix of a wet granulation process can become rubbery and unmanageable. A non-limiting list of disintegrants that are unsuitable in some embodiments of the formulations of the present disclosure includes: microcrystalline cellulose, pre-gelatinized starch, sodium starch glycolate, croscarmellose sodium, hydroxypropyl cellulose, swelling bentonite clays, cross-linked sodium carboxymethyl cellulose, polyvinylpyrrolidone, other modified starch, and modified cellulose, and combinations thereof, to name a few.

The formulations of the present disclosure may include further excipients and/or additives such as dyes, colorants, fillers, diluents, anti-caking agents, anti-foaming agents, sweeteners, flavorings, preservatives, antioxidants, stabilizers, and other auxiliary additives as may be desired by end-users.

In some embodiments of the present disclosure, the formulation comprises
 from about 20% to about 60% (w/w) of monensin;
 from about 1% to about 5% (w/w) of one or more surfactants selected from alkyl sulphates, sodium lauryl sulphate, sulphonates, sodium dodecylbenzene sulphonate, carboxylates, dioctyl sodium sulfosuccinate, quaternary ammonium salts, benzalkonium chloride, alkyl betaines, cocamidoalkyl betaines, polyoxyethylene glycol sorbitan alkyl esters, alkyl polyglucoside, polysorbates, alkoxylates, and combinations thereof;
 from about 1% to about 10% (w/w) of one or more binders selected from lignosulphonates, sodium lignosulphonate, and combinations thereof; and
 from about 10% to about 70% (w/w) of one or more fillers selected from lactose monohydrate, glucose, sucrose, sugars, mannitol, modified sugars, celluloses, magnesium silicate monohydrate, amorphous alumina silicate, and combinations thereof.

In some embodiments of the present disclosure, the formulation comprises
 from about 35 to about 55% (w/w) of monensin,
 from about 1% to about 5% (w/w) of alkyl polyglucoside,
 from about 5% to about 15% (w/w) of sodium lignosulphonate,
 from about 20% to about 40% (w/w) of magnesium silicate monohydrate, and
 from about 10% to about 30% (w/w) of amorphous alumina silicate.

In some embodiments of the present disclosure, the formulation comprises monensin at about 43% (w/w), alkyl polyglucoside at about 1% (w/w), sodium lignosulphonate at about 8% (w/w), and magnesium silicate monohydrate at about 18% (w/w), and amorphous alumina silicate at about 27% (w/w).

In some embodiments, residual water will be present in the formulation. After water is removed during the manufacturing process (drying), some residual water will remain. In some embodiments, up to about 2% (w/w) water is present in the formulation. In some embodiments, up to about 1% (w/w) water is present in the formulation.

The present disclosure provides granules of regular size and shape. As used herein, the term "regular size and shape" refers to granules that are closely sized and of reasonably consistent bulk density to enable them to be measured accurately by volume by the user. Volumetric measurement of the water dispersible granules is preferred by users for convenience rather than having to weigh the quantity required in a field use situation. Unlike most other granulation processes, the wet granulation process of the present disclosure produces granules of consistent size within a desired size range. The mean granule size can be altered by a change to the granulator configuration. In some embodiments, the typical granule product recovery is 90% minimum within the diameter size range of about 0.75 to about 1.75 millimeters. In some embodiments, the typical granule product recovery is 95% by weight minimum within the diameter size range of about 0.75 to about 1.75 millimeters. Within these ranges, the small amount of oversize and undersize granules are removed by screening and returned to the process. The shape and surface texture of the granules of the present disclosure are also important. The smooth textured granules provided flow more readily than rough textured angular chip type granules and are more resistant to attrition during transport and handling resulting in less dust generation.

Various embodiments of the present disclosure employ water dispersible granule formulations consisting of
 from about 40% to about 50% (w/w) monensin sodium,
 from about 1% to about 5% (w/w) alkyl polyglucoside,
 from about 5% to about 15% (w/w) sodium lignosulphonate,
 from about 20% to about 30% (w/w) magnesium silicate monohydrate,
 from about 10% to about 20% (w/w) amorphous alumina silicate, and
 water up to about 2% (w/w).

In some embodiments, the monensin sodium is present in the formulation at about 43% (w/w). In some embodiments, the alkyl polyglucoside is present in the formulation at about 1% (w/w). In some embodiments, the sodium lignosulphonate is present in the formulation at about 8% (w/w). In some embodiments, the magnesium silicate monohydrate is present in the formulation at about 18% (w/w). In some embodiments, the amorphous alumina silicate is present at about 27% (w/w). In some embodiments, the water is present in the formulation up to about 1% (w/w). In some embodiments, the water dispersible granules comprise a regular size and shape.

In some embodiments, the present disclosure provides a liquid formulation comprising a therapeutically effective amount of the formulation of the present disclosure dispersed in water or milk. In an embodiment, the liquid is water.

The formulations of the present disclosure are designed to be readily dispersible in water so that they can be added directly or indirectly (via a dispensing system such as a DOSATRON® or NutriDose) to animals' drinking water systems such as troughs, or so that they can be mixed with water and administered to animals via drench. If the formulation is added to the drinking water system of animals, upon addition to the water, the formulation disperses readily to provide a substantially stable solution of the monensin uniformly through the water, so that an animal receives a therapeutically effective amount of the monensin when drinking. Therefore, the present disclosure also provides various methods of administering the formulation of the present disclosure to animals. In some embodiments, the present disclosure provides a method of providing monensin to an animal comprising mixing a therapeutically effective amount of the formulation of the present disclosure with a liquid and orally administering the formulation to the animal. In some embodiments, the liquid is water. In some embodiments, the liquid is milk. In some embodiments, the animal is a ruminant. In some embodiments, the animal is a bovine. In some embodiments, the animal is a cow.

In some embodiments, the present disclosure provides a method of administering monensin to an animal comprising providing a therapeutically effective amount of the formulation of the present disclosure to the drinking water of the animal. In some embodiments, the animal is a ruminant. In some embodiments, the animal is a bovine. In some embodiments, the animal is a cow.

In some embodiments, the present disclosure provides a method of administering the formulation of the present disclosure to an animal, wherein the administration is via a water distribution system. In some embodiments, the animal is a ruminant. In some embodiments, the animal is a bovine. In some embodiments, the animal is a cow.

The present disclosure also provides various therapeutic methods. In some embodiments, the present disclosure provides a method of increasing milk production efficiency in an animal comprising administering to the animal in need thereof a therapeutically effective amount of the formulation of the present disclosure. As used herein, the term "increasing milk production efficiency" refers to an increase in animal production of marketable solids per unit of feed intake. In some embodiments, the animal is a ruminant. In some embodiments, the animal is a bovine. In some embodiments, the animal is a cow.

In some embodiments, the present disclosure provides a method of treating or preventing ketosis in an animal comprising administering to the animal in need thereof a therapeutically effective amount of the formulation of the present disclosure. "Preventing" refers to reducing the likelihood that the patient will incur or develop any of the pathological conditions described herein and includes prophylactic administration. The term "preventing" is particularly applicable to an animal that is susceptible to the particular pathological condition. "Treating" refers to mediating a disease or condition and preventing, reversing the clinical effects of the disease, mitigating its further progression, or ameliorating the symptoms associated with the disease or condition. In some embodiments, the animal is a ruminant. In some embodiments, the animal is a bovine. In some embodiments, the animal is a cow.

In some embodiments, the present disclosure provides a method of treating or preventing bloat in an animal comprising administering to the animal in need thereof a therapeutically effective amount of the formulation of the present disclosure. As used herein, the term "bloat" refers to a highly harmful condition that results from excess gas accumulation in the rumen. The afflicted animal is unable to dispose of the gas by eructation due to the entrapment of gas in a stable foam. Foaminess of the rumen is a predisposing factor for bloat. In some embodiments, the animal is a ruminant. In some embodiments, the animal is a bovine. In some embodiments, the animal is a cow.

In some embodiments, the formulations of the present disclosure are administered to a ruminant. As used herein, the term "ruminant" refers to an even-toed hoofed animal that has a complex 3-chamber or 4-chamber stomach and which typically re-chews what it has previously swallowed. Some non-exhaustive examples of ruminants include bovines, sheep, goats, oxen, muskox, llamas, alpacas, guanicos, deer, bison, antelopes, camels, and giraffes. In some embodiments, the ruminant is a bovine. As used herein, the term "bovine" refers to cattle, cow, bison, African buffalo, water buffalo, yak, and antelope, to name a few. In some embodiments, the animal is a cow. In some embodiments, the ruminant is a goat.

In some embodiments, the present disclosure provides a formulation for use in therapy. In some embodiments, the present disclosure provides a formulation for use in providing monensin to an animal comprising mixing a therapeutically effective amount of the formulation with a liquid and orally administering the formulation to the animal. In some embodiments, the liquid is water or milk. In some embodiments, the present disclosure provides a formulation for use in administering monensin to an animal comprising providing a therapeutically effective amount of the formulation to the drinking water of the animal. In some embodiments, the present disclosure provides a formulation for use in increasing milk production efficiency in an animal comprising administering to the animal in need thereof a therapeutically effective amount of the formulation. In some embodiments, the present disclosure provides a formulation for use in treating or preventing ketosis in an animal comprising administering to the animal in need thereof a therapeutically effective amount of the formulation. In some embodiments, the present disclosure provides a formulation for use in treating or preventing bloat in an animal comprising administering to the animal in need thereof a therapeutically effective amount of the formulation. In some embodiments, the animal is a ruminant. In some embodiments, the animal is a cow. In some embodiments, the administration is via a water distribution system.

In some embodiments, the present disclosure provides the use of a formulation for the manufacture of a medicament for use in providing monensin to an animal comprising mixing a therapeutically effective amount of the formulation with a liquid and orally administering the formulation to the animal. In some embodiments, the liquid is water or milk. In some embodiments, the present disclosure provides the use of a formulation for the manufacture of a medicament for use in administering monensin to an animal comprising providing a therapeutically effective amount of the formulation to the drinking water of the animal. In some embodiments, the present disclosure provides the use of a formulation for the manufacture of a medicament for use in increasing milk production efficiency in an animal comprising administering to the animal in need thereof a therapeutically effective amount of the formulation. In some embodiments, the present disclosure provides the use of a formulation for the manufacture of a medicament for use in treating or preventing ketosis in an animal comprising administering to the animal in need thereof a therapeutically effective amount of the formulation. In some embodiments, the present disclosure provides the use of a formulation for the manufacture of a medicament for use in treating or preventing bloat in an animal comprising administering to the animal in need thereof a therapeutically effective amount of the formulation. In some embodiments, the animal is a ruminant. In some embodiments, the animal is a cow. In some embodiments, the administration is via a water distribution system.

As will be appreciated by those of ordinary skill in the art, the animals will drink the treated water ad libitum, but it is contemplated that they will receive substantially a therapeutically effective amount of the monensin based on the average amount of water that an animal generally drinks per day. It is therefore important that the monensin remains in a substantially stable solution in the drinking water and in an acceptable concentration. It is also important that the monensin remains uniformly dispersed through the body of drinking water for a sufficient period of time in order to provide a safe and practical form of treatment The present disclosure also provides a process for the manufacture of water dispersible monensin granules. The process of the present disclosure produces high single pass recovery of granules of regular size and shape. As used herein, the phrase "high single pass recovery" means that only a single granulation step of the mixed product (i.e., monensin plus excipients) is required in the process of the present disclosure, as at least about 90%, and more preferably at least about 95%, by weight, of the granules are within the desired size range. The water dispersible granules produced by the process of the present disclosure are of such high quality that the granules do not need to undergo any granulation steps in addition to the single requisite granulation step. In some embodiments, a minimum of 90% of the granules are produced by the process of the present disclosure within the size range of 0.75 to 1.75 millimeters with a maximum of 10% of oversize and undersize granules removed by screening and returned to the granulation process.

In some embodiments, there are two pre-process steps—a milling step and a mixing step—and one process step of granulation.

The pre-process milling step involves milling of the monensin to the desired particle size. We have found that the particle size of the monensin is important in order to produce a water dispersible granule formulation with appropriate flowability, friability, dispersability, and re-suspensibility characteristics. The milling step can be carried out using a wet milling or dry milling process. An example of a wet milling process suitable for the present disclosure is bead milling. Dry milling processes that are suitable for the present disclosure include air milling, air jet milling, micronizing, and fluid energy milling, to name a few. It is envisioned that any suitable way of dry or wet milling monensin to the desired particle size may be utilized according to the present disclosure.

Once the monensin has been milled to the desired particle size, the milled product can be taken away as an intermediate product (e.g., post mill product) for subsequent use elsewhere for blending. In some embodiments, the milled monensin should be mixed with all of the excipients after milling. In some embodiments, this is done by adding small portions of each of the components to a mixing vessel alternatively and sequentially and blending until a homogenous mixture is produced. Blending time will vary depending on batch size. A batch size of about 45 kg requires at least 5 minutes of blending. An Interrupted Ribbon Blender is an example of mixing equipment suitable for the present disclosure.

Once the components of the formulation have been mixed, the mixed product is then granulated. The granulation step can be carried out using only a wet granulation process. Wet granulation is preferred, as it has been found to produce the most successful formulation in terms of the desired characteristics of the resulting water dispersible granule (i.e., granule size distribution, strength and friability of granules, water dispersability performance, and stability of the active ingredient both in its granule form and upon its dispersion in water). Examples of wet granulation processes that are suitable for the present disclosure include pan and drum granulation processes, extrusion, and spray drying, to name a few. Any type of wet granulation process is contemplated by the present disclosure, A Jackson & Crockett No. 4 Granulator is an example of wet granulation equipment suitable for the present disclosure. Dry granulation processes are not suitable for the present disclosure. The use of high pressure dry compaction leads to the production of a dense cake and breaking the a dense cake down mechanically results in the production of angular chips of random size and shape.

Once the fine powder has been put through the wet granulator to form the granules, there is an optional sieving step to remove larger particles and to ensure that the resulting granules are of a consistent size. The larger particles can then be returned to the granulator to be processed again. A Vibratory Sieve is an example of sieve equipment suitable for the present disclosure.

Various embodiments of the present disclosure utilize processes for the preparation of the formulation of the present disclosure comprising granulating the monensin with the surfactant, the hinder, and the filler to form granules using a wet granulation process, wherein the monensin has been milled to a mean particle size diameter of less than about 30 microns before the granulating. In some embodiments, the wet granulation process is a low pressure wet granulation process. In some embodiments, the process further comprises sieving the granules. In some embodiments, the sieving step is a dry process. In some embodiments, the sieving step is a wet process. In some embodiments, the monensin is milled by a wet milling process before the granulating. In some embodiments, the monensin is milled by a dry milling process before the granulating. In some embodiments, the monensin has a mean particle size diameter from about 1 to about 25 microns and about 80% of the monensin particles are no more than about 20 microns. In some embodiments, the monensin has a mean particle size diameter from about 5 to about 20 microns. In some embodiments, the monensin has a mean particle size diameter from about 10 to about 15 microns. In some embodiments, the milled monensin has a mean particle size diameter from about 8 to about 12 microns. In some embodiments, the water dispersible granules comprise a regular size and shape.

Non-limiting examples of the formulations of the present disclosure will now be described, and the formulations in each of these examples can be prepared by the processes described hereinabove.

EXAMPLE 1

| Component | Function of Component | Concentration (% w/w) |
|---|---|---|
| Monensin Sodium Milled | Ionophore Antibiotic | 43.48 |
| AGNIQUE ® PG 8107 | Surfactant/Wetting Agent | 2.00 (1.4 dry) |
| Ultrazine NA | Binder/Disperser | 12.00 |
| Talc SF 15 | Filler/Anticaking agent/Lubricant/Helps Dispersion | 24.12 |
| HARBORLITE ® 200 | Filler/Helps dispersion | 18.00 |

\* Granulation water is utilized in the batch as a granulating aid/medium at 28.0 Granulation Water Parts per Hundred (PPH).

EXAMPLE 2

| Component | Function of Component | Concentration (% w/w) |
|---|---|---|
| Monensin Sodium Milled | Ionophore Antibiotic | 43.48 |
| AGNIQUE ® PG 8107 | Surfactant/Wetting Agent | 2.00 (1.4 dry) |
| Ultrazine NA | Binder/Disperser | 10.00 |
| Talc SF 15 | Filler/Anticaking agent/Lubricant/Helps Dispersion | 26.12 |
| HARBORLITE ® 200 | Filler/Helps dispersion | 18.00 |

\* Granulation water is utilized in the batch as a granulating aid/medium at 27.5 Granulation Water Parts per Hundred (PPH).

EXAMPLE 3

| Component | Function of Component | Concentration (% w/w) |
|---|---|---|
| Monensin Sodium Milled | Ionophore Antibiotic | 43.48 |
| AGNIQUE ® PG 8107 | Surfactant/Wetting Agent | 2.00 (1.4 dry) |
| Ultrazine NA | Binder/Disperser | 9.00 |
| Talc SF 15 | Filller/Anticalking agent/Lubricant/Helps Dispersion | 27.12 |
| HARBORLITE ® 200 | Filler/Helps dispersion | 18.00 |

\* Granulation water is utilized in the batch as a granulating aid/medium at 28.0 Granulation Water Parts per Hundred (PPH).

EXAMPLE 4

| Component | Function of Component | Concentration (% w/w) |
|---|---|---|
| Monensin Sodium Milled | Ionophore Antibiotic | 43.48 |
| AGNIQUE ® PG 8107 | Surfactant/Wetting Agent | 2.00 (1.4 dry) |
| Ultrazine NA | Binder/Disperser | 8.00 |
| Talc SF 15 | Filler/Anticaking agent/Lubricant/Helps Dispersion | 28.12 |
| HARBORLITE ® 200 | Filler/Helps dispersion | 18.00 |

\* Granulation water is utilized in the batch as a granulating aid/medium at 29.5 Granulation Water Parts per Hundred (PPH).

EXAMPLE 5

| Component | Function of Component | Concentration (% w/w) |
|---|---|---|
| Monensin Sodium Milled | Ionophore Antibiotic | 43.48 |
| AGNIQUE ® PG 8107 | Surfactant/Wetting Agent | 2.00 (1.4 dry) |
| Ultrazine NA | Binder/Disperser | 7.00 |
| Talc SF 15 | Filler/Anticaking agent/Lubricant/Helps Dispersion | 29.12 |
| HARBORLITE ® 200 | Filler/Helps dispersion | 18.00 |

\* Granulation water is employed in the batch as a granulating aid/medium at 32.0 Granulation Water Parts per Hundred (PPH).

EXAMPLE 6

| Component | Function of Component | Concentration (% w/w) |
|---|---|---|
| Monensin Sodium Milled | Ionophore Antibiotic | 43.48 |
| AGNIQUE ® PG 8107 | Surfactant/Wetting Agent | 1.40 |
| Ultrazine NA | Binder/Disperser | 8.50 |
| Talc SF 15 | Filler/Anticaking agent/Lubricant/Helps Dispersion | 27.62 |
| HARBORLITE ® 200 | Filler/Helps dispersion | 18.00 |
| Residual Water | Water is removed during the manufacturing process (drying) although some residual water will remain | Approx. 1 |

The above example formulations are suitable for addition to the drinking water system of animals to be treated, or they can be mixed with water or milk to provide a drench formulation.

Study 1: Compatibility

Studies can be conducted to test the compatibility of the formulation of Example 1 with various materials that are often added to the drinking water of dairy cattle. The materials that can be tested include zinc sulphate heptahydrate, magnesium chloride hexahydrate, copper sulphate pentahydrate, and Bloatenz Plus. These studies illustrate that the formulation of Example 1 demonstrates desirable compatibility with all the salts and Bloatenz Plus. The compatibility is demonstrated by none of the mixtures showing any signs of flocculation, excessive precipitation, or other adverse reaction. The magnesium chloride solution appears to provide some buoyancy to the granules and dispersed particles in the initial stales of the trial.

Study 2: Process Development

A 1.3 kg laboratory batch of the formulation of Example 1 is prepared via a laboratory "Grantrol" granulator for use in a short term (2 months) stability study and compatibility testing program. The Grantrol granulator process is a process by which a continuously fed granulator is used to convert an intimate water wet mixture of technical grade active ingredient, surfactants or other ingredients where applicable into granules of consistent size and density during a single pass.

The Ultrazine NA and AGNIQUE® PG 8107 are applied in solution with part of the water used for granulation in the proportions set out in TABLE 1.

TABLE 1

| Ingredient | % w/w |
| --- | --- |
| Ultrazine NA | 36.00 |
| AGNIQUE ® PG 8107 | 6.00 |
| Water 50 deg. C. | 58.00 |

The dry ingredients are blended and the surfactant solution is added at the rate of 33.33 g/100 g dry and thoroughly blended. Water is added incrementally and blended until a damp evenly colored pre-mix of appropriate consistency is formed. The damp premix is passed through the granulator twice for stress processing. The quantity of water is about right on first pass, but marginally too much at second pass. It granulates at a fast rate. The extrudates are cohesive and break down well. The wet granules are dried at 45° C. and screened through a 0.750 mm and 1.7 mm screens. There is very little oversize or fines produced, normally less than about 5%, and more preferably, less than about 4.6% by weight. 1.24 kg is recovered after losses to granulator and screening. Time to disperse at 20° C. is 65 seconds, which is well within specification and the visual quality of the suspension is excellent. The results are provided in TABLE 2.

TABLE 2

| Test | | Results |
| --- | --- | --- |
| Time to disperse | | 65 seconds |
| Suspensibility | | 82% total solids |
| Wet sieve residue | 150 μm | 0.003% |
| (% w/w retained, | 75 μm | 0.055% |
| cumulative) | 45 μm | 0.660% |
| Bulk density | Loose | 501.5 g/L |
| | Tapped | 575.5 g/L |
| pH | | 7.37 |
| Assay | | 433 mg/g |
| | | (43.3% w/w) |
| LOD | | 1.1% |
| Resistance to Attrition | | 99.1% |
| Wettabillity | Without swirling | 40 seconds |
| | With swirling | 4-5 seconds |

A 5 kg batch of the formulation of Example 1 is manufactured to test the manufacturing process before progressing to a larger scale batch. The viscous liquid formed by dissolving all of the Ultrazine NA in a substantial part of the granulation water may not be able to be sprayed effectively through the preferred nozzles of the pilot plant blender liquid delivery system. Allowing only 3 kg additional water per 100 kg dry pre-mix does not provide adequate flexibility for adjustment of water level in the commercial process as may be required to compensate in variations in particle size and absorptive capacity of powder raw materials as well as the ambient conditions (temperature and humidity).

A trial batch of 45 kg of the formulation of Example 6 can be produced. For instance, all raw materials are pre-weighed as specified in TABLE 3. Next, 1.00 kg of distilled water (ambient) and AGNIQUE® PG 8107 can be added to a clean 20 L pail. Using a mechanical stirrer with an impellor, the AGNIQUE® PG 8107 is dispersed. Then, the HARBORLITE® 200, Ultrazine NA, Talc Superfine 15, and monensin sodium milled, as specified in TABLE 3, are added to an interrupted ribbon blender. Next, the interrupted ribbon blender is turned on and blended for approximately 5 minutes. While blending, 1.80 kg of AGNIQUE® PG 8107 Solution is pumped into the interrupted ribbon blender through spray nozzles. Next, the AGNIQUE® PG 8107 Solution container, lines, and nozzles are flushed with approximately 9 kg distilled water into the interrupted ribbon blender while blending. Additional distilled water may be added if necessary. Blending of the ingredients is continued until a homogenous mix is achieved. At the completion of blending, the damp premix is transferred onto a blender conveyor. Next, the granulator is filled with premix, the premix is passed through the granulator and a conditioner/compactor, and the premix is put in a dryer container. Then, the dryer container is placed into the fluid bed dryer, and the premix is dried at 50° C. until the outlet temperatures reach 50° C. At completion of drying, the dryer and shake socks are turned off, the drying trolley is removed, and the granules are examined for the presence of dust. Next, the container is removed from the dryer and wheeled around to the container discharge hopper. The hopper is fully discharged into a storage hopper. Sieving is commenced and the product is filled into 20 L pails until the hopper is empty.

TABLE 3

| Ingredient | Amount Required (kg) |
| --- | --- |
| AGNIQUE ® PG 8107 | 2.00 |
| HARBORLITE ® 200 | 8.10 |
| Uttrazine NA | 3.83 |
| Talc Superfine 15 | 12.43 |
| Monensin Sodium Milled | 19.57 |

The following can be concluded from this trial batch. The product granulates well through the Jackson & Crockett No. 4 Granulator with no agglomeration occurring. This indicates the amount of Ultrazine at 8.5% (w/w) and quantity of water used was acceptable. However, the formation of a few agglomerates in the conditioner did indicate slightly too much water had been used. Their formation could have been compensated for if the residence time in the conditioner had been reduced. A setting of 3.5 on the fluid bed dryer appears acceptable and does not cause excessive dust formation. The monensin homogeneity within the blended damp premix is considered to be acceptable indicating the ribbon blender is capable of producing a homogeneous blend prior to granulation. The monensin homogeneity within the final dried product is considered to be acceptable indicating the processing that occurs post the ribbon blender does not have a negative impact on homogeneity. The vibratory sieve screen sizes used appeared suitable for the removal of dust and agglomerates without the loss of good product. It is recommended that the amount of water should be reduced by approximately 300 g for a 45 kg batch.

Study 3: Stability

Accelerated stability trials are carried out to determine the acceptable shelf life of a water dispersible monensin granule formulation of the present disclosure comprising about 43% (w/w) active monensin. A 1.3 kg laboratory batch of the formulation described in Example 1 is placed on a 60 day 54° C. accelerated stability study. The study is designed to test how stable the formulation is under extreme conditions. All results comply with the tentative stability specifications or targets indicating that the formulation is stable and could survive longer periods under less extreme conditions. The results are provided in TABLE 4.

Assuming the product produced commercially has a starting content of 400 mg/g monensin sodium, the results indicate the product will still be within the tentative stability specification at the end of shelf life as the reduction is less than 15% of the 0 day result (i.e., within 85 to 115% of 0 days). The assumption above is that 60 days at 54° C. is equivalent to 36 months at 30° C.

TABLE 4

| Test | Tentative Stability Specification | 0 days | 30 days @ 54° C. | 60 days @ 54° C. |
|---|---|---|---|---|
| Time to disperse (seconds) | NMT 90 seconds | 65 | 60 | 70 |
| Suspensibility (% total solids) | NLT 60% active suspended | 82 | 81 | 76 |
| Suspensibility (% active) | NLT 60% active suspended Target | | | |
| Wet sieve 150 μm residue 75 μm (% w/w 45 μm retained, cumulative) | 0.3% max 2.0% max 3.0% max | 0.003 0.055 0660 | 0.006 0.067 0.683 | 0.004 0.076 0.687 |
| Monensin Sodium (mg/g) | 340 to 460 mg/g | 433 | 391 | 388 |
| Monensin Sodium (as % of 0 days) | Target: 85 to 115% of 0 days | 100 | 90.3 | 89.6 |
| Wettability without swirling (seconds) | Target NMT 120 seconds | 40 | NT | 25 |
| Wettability with swirling (seconds) | Target NMT 120 seconds | 4-5 | NT | 5-6 |
| LOD (% w/w) | NMT 30% w/w | 1.1 | 0.9 | 0.8 |

The 45 kg trial batch of the formulation described in Example 1 is placed on a 14 days 54° C. accelerated stability study. All results comply with the tentative stability specifications or targets and are comparable to the 60 day study above. The results are provided in TABLE 5.

TABLE 5

| Test | Tentative Stability Specification | 0 days | 14 days @ 54° C. |
|---|---|---|---|
| Time to disperse (seconds) | NMT 90 seconds | 75 | 85 |
| Suspensibility (% total solids) | NLT 60% active suspended Target | 81 | 75 |
| Wet sieve 150 μm residue (% w/w 75 μm retained, 45 μm cumulative) | up to 0.3% max up to 2.0% max up to 3.0% max | 0.004 0.006 0.030 | 0.009 0.019 0.287 |
| Wettability without swirling (seconds) | Target NMT 120 seconds | 25 | 15 |
| Wettability with swirling (seconds) | Target NMT 120 seconds | 2 | 3 |

We claim:
1. A water dispersible granule formulation comprising from about 5% to about 80% (w/w) of monensin;
from about 1% to about 20% (w/w) of one or more surfactants selected from alkyl sulphates, sodium lauryl sulphate, sulphonates, sodium dodecylbenzene sulphonate, carboxylates, dioctyl sodium sulfosuccinate, quaternary ammonium salts, benzalkonium chloride, alkyl betaines, cocamidoalkyl betaines, polyoxyethylene glycol sorbitan alkyl esters, alkyl polyglucoside, polysorbates, alkoxylates, and combinations thereof;
from about 1% to about 30% (w/w) of one or more binders selected from lignosulphonates, sodium lignosulphonate, and combinations thereof;
from about 1% to about 90% (w/w) of one or more fillers selected from lactose monohydrate, glucose, sucrose, sugars, mannitol, modified sugars, celluloses, magnesium silicate monohydrate, amorphous alumina silicate, and combinations thereof; and
water up to about 2% (w/w); wherein the formulation does not comprise a disintegrant.

2. The formulation of claim 1, comprising
from about 35 to about 55% (w/w) of monensin,
from about 1% to about 5% (w/w) of alkyl polyglucoside,
from about 5% to about 15% (w/w) of sodium lignosulphonate,
from about 20% to about 40% (w/w) of magnesium silicate monohydrate, and
from about 10% to about 30% (w/w) of amorphous alumina silicate.

3. The formulation of claim 1, comprising monensin at about 43% (w/w), alkyl polyglucoside at about 1% (w/w), sodium lignosulphonate at about 8% (w/w), and magnesium silicate monohydrate at about 18% (w/w), and amorphous alumina silicate at about 27% (w/w).

4. A method of treatment comprising providing a therapeutically effective amount of a water dispersible granule formulation to a volume of drinking water of an animal;
wherein the water dispersible granule formulation comprises:
from about 35 to about 55% (w/w) of monensin,
from about 1% to about 5% (w/w) of alkyl polyglucoside,
from about 5% to about 15% (w/w) of sodium lignosulphonate,
from about 20% to about 40% (w/w) of magnesium silicate monohydrate, and
from about 10% to about 30% (w/w) of amorphous alumina silicate;
wherein the formulation does not comprise a disintegrant.

5. The method of claim 4, wherein the treatment further comprises increasing milk production efficiency.

6. The method of claim 4, wherein the treatment further comprises treating or reducing occurrence of ketosis.

7. The method of claim 4, wherein the treatment further comprises treating or reducing occurrence of bloat.

* * * * *

UNITED STATES PATENT AND TRADEMARK OFFICE
CERTIFICATE OF CORRECTION

PATENT NO. : 10,117,849 B2
APPLICATION NO. : 15/556654
DATED : November 6, 2018
INVENTOR(S) : Kim Ewing Melville Agnew et al.

Page 1 of 1

It is certified that error appears in the above-identified patent and that said Letters Patent is hereby corrected as shown below:

In the Claims

Column 18 Line 22: In Claim 2, delete "35" and insert -- 35% --, therefor.

Column 18 Line 39: In Claim 4, delete "35" and insert -- 35% --, therefor.

Signed and Sealed this
Fifteenth Day of January, 2019

Andrei Iancu
*Director of the United States Patent and Trademark Office*